(12) United States Patent
Logan (10) Patent No.: US 8,417,347 B2
(45) Date of Patent: Apr. 9, 2013

(54) METHOD FOR ACHIEVING FACIAL TONING USING SELECTIVELY APPLIED GALVANIC CURRENT

(76) Inventor: Elizabeth Logan, Wilmington, NC (US)

( * ) Notice: Subject to any disclaimer, the term of this patent is extended or adjusted under 35 U.S.C. 154(b) by 0 days.

(21) Appl. No.: 13/106,541

(22) Filed: May 12, 2011

(65) Prior Publication Data

US 2012/0290044 A1    Nov. 15, 2012

(51) Int. Cl.
*A61N 1/00*    (2006.01)
(52) U.S. Cl.
USPC ............................................................ 607/48
(58) Field of Classification Search .................... 607/48, 607/74; 604/20
See application file for complete search history.

(56) References Cited

U.S. PATENT DOCUMENTS

| | | | |
|---|---|---|---|
| 4,957,480 A * | 9/1990 | Morenings | 604/20 |
| 2008/0195181 A1 * | 8/2008 | Cole | 607/74 |

\* cited by examiner

*Primary Examiner* — Niketa Patel
*Assistant Examiner* — Minh Duc Pham
(74) *Attorney, Agent, or Firm* — William J. Sapone (57) ABSTRACT

A method of toning the facial muscles and tissues in selected target areas involves applying predetermined galvanic currents, frequencies, and polarities to the target areas in specific patters and with particular repetitions and movements selected to provide enhanced cosmetic effects, such as reduced lines and wrinkles, reduced depth of folds, and improved circulation to promote health and vitality.

18 Claims, 9 Drawing Sheets

METHOD FOR ACHIEVING FACIAL TONING USING SELECTIVELY APPLIED GALVANIC CURRENT

TECHNICAL FIELD

The present invention relates to a method of toning the muscles underlying the human face and the overlying facial tissues using locally selectively applied galvanic current, preferably while applying a liquid solution of positively and negatively charged particles for nourishing the tissue.

BACKGROUND

The skin of a human being is the largest organ and comprises about one-sixth of the total body weight. It protects the human being from ultraviolet rays; from mechanical, chemical and thermal injuries; from bacterial invasions and from dehydration and water penetration.

The skin is also the largest sensory organ, and contains nerve endings for touch, pain, pressure and temperature.

The three main layers of the skin comprise the epidermis, which is dry dead skin, nonvascular; the dermis, which is flexible, elastic and vascular tissue; and the subcutaneous, which is mostly fatty tissues.

The layers of the epidermis comprise the stratum corneum, which is a horny layer, made up of flattened dead cells; the stratum lucidum, which is a thin homogeneous layer; the stratum grandulosum which are granules effecting keratinization; the stratum spinosum, which are cells in the growing process; and the stratum germinativum, which is where new cells are produced and is also the location of melanin, a dark pigment.

The layers of the dermis comprise the stratum papillare, which are small, sensitive vascular papillare; and the stratum reticulare, which is the connective tissue composed of collagen.

Nutrition to the skin is achieved by diffusion from the dermis to the stratum germinativum layer of the epidermis. There are two methods of diffusion: (1) diffusion of a liquid through a cell wall; and (2) diffusion of molecules through cell wall pores. Any substance, such as water, the molecules of which are smaller than the pores, can pass through those pores. The factors that determine the rate of diffusion comprise: (1) concentration gradient, i.e., from higher to lower concentration; (2) pressure gradient, i.e., from higher to lower pressure; and electrical gradient, i.e., ions are attracted or repelled by positive (+) or negative (−) charges and thus, are caused to move across a membrane.

In U.S. Pat. No. 4,957,480, a method of toning the muscles and tissues of the human face is described which is directed to stimulating the motor nerves to cause contraction of the muscles of the human face by use of a pair of electrodes connected to a source of predetermined galvanic current and operating at a predetermined frequency and predetermined polarity, and continually moistening the tips of the electrodes with a liquid solution of positively and negatively charged particles and pressing the moistened tips against the skin of the human face at two different positions and while pressed against the skin moving in a predetermined manner at least one of the moistened tips relative to the other to a still different position as the charged particles penetrate into the epidermis and dermis of the human face.

While generally useful for effecting muscle toning, it was found that it is difficult to achieve satisfactory results using only the techniques described in this patent, particularly with specific muscle groups, and the search continues for improved methods for achieving facial toning over a broad spectrum of muscle tissue. In addition, it has been discovered that other cosmetic benefits beyond facial toning, in terms of the look, color, suppleness and vitality of the facial tissue can be enhanced according to the present invention.

SUMMARY OF THE INVENTION

It is an object of the present invention to provide improved methods for effecting facial skin and muscle toning, and to provide other cosmetic and therapeutic effects.

These and other objects of the present invention are achieved by a method of toning the muscles and tissues of the human face comprising stimulating specific motor nerves to cause contraction of selected muscles of the human face by providing a pair of electrodes connected to a source of predetermined galvanic current, providing mean for operating the source at multiple user selected frequencies, pressing the pair of electrodes against the skin of the human face at two preselected positions adjacent a specific target area and while pressed against the skin, moving one electrode in a first programmed pattern while either holding the second electrode in position or moving the other electrode in a second programmed pattern adjacent to the specific preselected target tissue. The method further includes moving the tips relative to each other in the preselected pattern multiple times, while continually moistening the tips of the electrodes with a liquid solution of positively and negatively charged particles. The electrode tips are additionally operated at a plurality of frequencies selected for promoting the specific effect sought. Thus, the underlying selected target area undergoes variably stimulated contraction in the preselected pattern, while charged particles are either delivered into or withdrawn from the targeted tissue.

Preferable, the source delivers a galvanic current in a range of about 160 to about 640 microamperes and at frequencies selected from the range of about 3 to about 10 hertz. Polarity altering from positive to negative should be provided for a duration ranging from about 1 to about 4 seconds for each of the polarities.

One exemplary method of the invention is directed to achieving the effect of draining the target area beneath the eye which comprises placing one electrode at the lateral corner just below the eye, placing the second electrode at a medial inferior corner just below the eye and with very light pressure moving the first electrode towards the midline located electrode and then back to the starting position with no pressure, and repeating, each pass to be completed within about 0.5 seconds, the source operating at a galvanic current of about 160 microamps, and at a frequency of about 10 Hz, and also with alternating tip polarity. This is done for about 0.5-2 minutes, and comprises a first session. A second session identical to the first is performed after a rest period. Thereafter, each additional session would be identical in terms of electrode placement and strokes, but the source would be operated at a galvanic current of about 320 microamps, and at a frequency of about 7 Hz.

This stroke in essence sweeps across the skin, with the effect of moving or draining excess fluid from under the eye area towards the nasal duct, promoting a reduction of swelling and discoloration under the eye area.

Other features of the present invention are discussed further below.

BRIEF DESCRIPTION OF THE DRAWINGS

The invention will be described in connection with the accompanying drawings, in which.

DETAILED DESCRIPTION OF THE INVENTION

The present invention is directed to specific methods for effecting facial skin and muscle toning, and to provide other cosmetic and/or therapeutic effects. It was discovered that using preselected movement pattern while having a pair of charged electrodes in contact with the facial skin can provide enhanced toning, as well as providing cosmetic effects.

In particular, methods for toning the muscles and tissues of the human face comprise stimulating specific motor nerves to cause contraction of selected muscles of the human face by providing a pair of electrodes connected to a source of predetermined galvanic current. Mean for operating the source at multiple user selected frequencies are provided which are operated in particular ways to achieve specific results on various target areas of the face. The pair of electrodes are generally pressed against the skin of the human face at two preselected positions adjacent a specific target area. While pressed against the skin, one electrode is moved in a first programmed pattern while the other electrode is either held in place or moved in a second programmed pattern adjacent to the specific preselected target tissue. Typically, the electrode tips are moved relative to each other in the preselected pattern multiple times. The tips are supplied with a conductive liquid and are continually moistened with the liquid to provide positively and negatively charged particles. The electrode tips are additionally operated at a plurality of frequencies selected for promoting the specific effect sought. The wave forms developed may also vary, such as providing a square wave pattern, round wave pattern or line pattern. Thus, the underlying selected target area undergoes variable stimulation in the preselected pattern, while charged particles are either delivered into or withdrawn from the targeted tissue.

In a first embodiment of the invention, a method for draining fluid from beneath the eye is disclosed. This is a very sensitive area and many techniques have been proposed for reducing fluid and also for reducing darkness under the eyes. This method was developed to address those specific issues.

This method involves placing one electrode at the lateral corner just below the eye, placing the second electrode at a medial inferior corner just below the eye and with very light pressure moving the first electrode towards the midline located electrode and then back to the starting position with no pressure, and repeating, each complete back and forth pass to be completed within about 0.5 seconds, with the source operating at a galvanic current of about 160 microamps, and at a frequency of about 10 Hz, and also with alternating tip polarity.

Figure 1A:
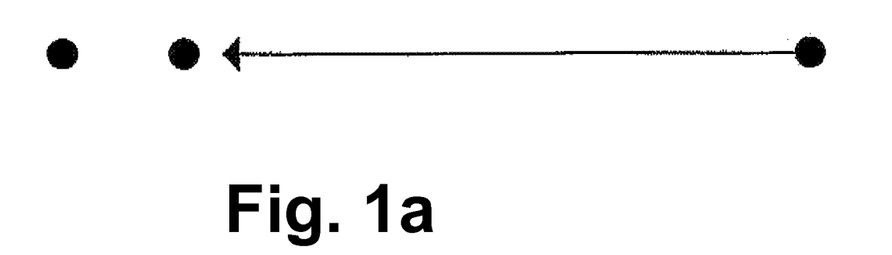
FIG. 1a is a view of an exemplary application pattern for promoting sinus draining and FIG. 1b is view of a human face with the arrows illustrating the pattern as practiced for promoting sinus draining.
Figure 1B:
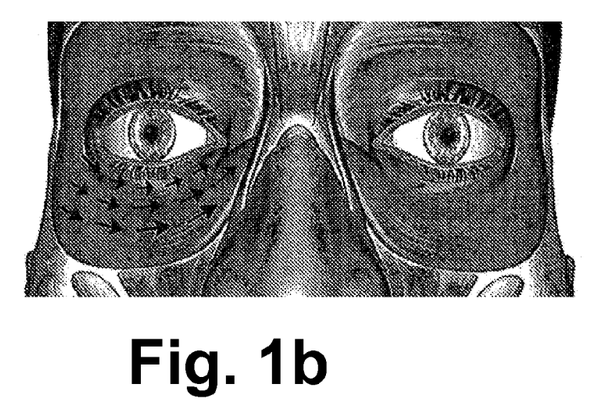

FIG. 1a is an illustrative view of this application pattern. The dots represent the initial positions of the moistened tips of the two electrodes, and the arrows illustrate the path and extent of movement of one or both moistened tips relative to a muscle or to the skin of the face. If there is no arrow leading from a dot, then that particular tip remains fixed in place. FIG. 1b illustrates the pattern in practice.

The above sequence is repeated for from 1-3 minutes and comprises a first session. A second session identical to the first is performed after a rest period. Thereafter, each additional session would be identical in terms of electrode placement and strokes, but the source would be operated at a galvanic current of about 320 microamps, and at a frequency of about 7 Hz.

This stroke in essence sweeps across the skin, with the effect of moving or draining excess fluid from under the eye area towards the nasal duct, promoting a reduction of swelling and discoloration under the eye area.

In another embodiment of the invention, a method for reducing crows feet at the corner of the eyes is disclosed which tones the Temporalis.

Figure 2A:
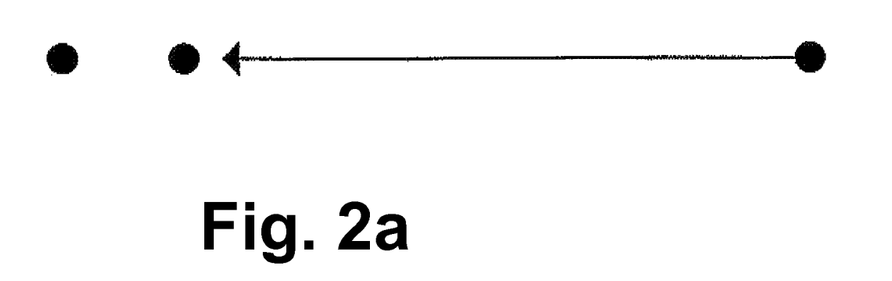
FIG. 2a is a view of an exemplary application pattern for promoting toning of the temporalis and FIG. 2b is a view of a human head with the arrows illustrating the pattern as practiced for promoting toning of the temporalis.
Figure 2B:
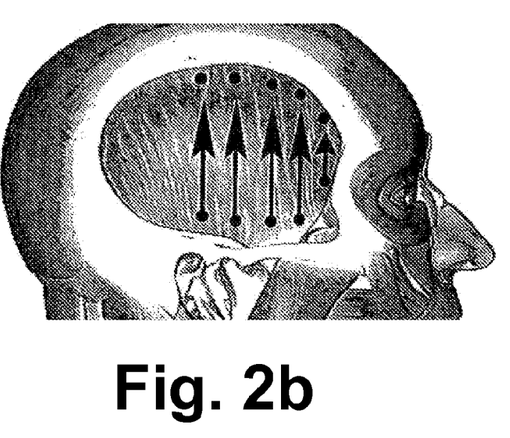

This method involves placing one electrode at the origin of the temporalis muscle and one at the insertion of the muscle. The electrodes are held in position for about 6 seconds, then one travel towards the other with light pressure at a speed of about 0.5 inches per second, until the electrodes are about 0.5 inches apart with a fold of tissue created therebetween. The tips are then held in that position for about 4 seconds. The above is repeated at least three more times with the electrodes moved each time about 0.25 inches from their prior original position. During the application, the source is operated at a galvanic current of about 160 microamps, and at a frequency of about 10 Hz, and also with alternating tip polarity. FIG. 2a is an illustrative view of this application pattern. This comprises a first session. A second session identical to the first is performed after a rest period. Thereafter, sessions 3 and 4 would be identical in terms of electrode placement and strokes, but the source would be operated at a galvanic current of about 320 microamps, and at a frequency of about 7 Hz. Each session thereafter would be identical in terms of electrode placement and strokes but the source would be operated at a galvanic current of about 640 microamps and a frequency of about 3 Hz. FIG. 2b illustrates the pattern in practice.

This stroke in essence lessens or smoothes the crows feet and also raises the angle of the eyes.

In another embodiment of the invention, a method for toning the area around the nasolabial fold is disclosed.

Figure 3A:
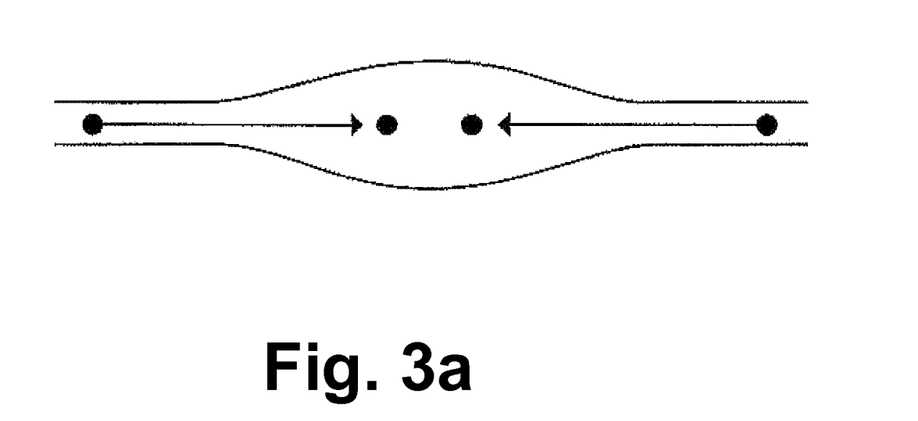
FIG. 3a is a view of an exemplary application pattern for promoting nasolabial fold toning and FIG. 3b is view of a human face with the arrows illustrating the pattern as practiced for promoting nasolabile fold toning.
Figure 3B:
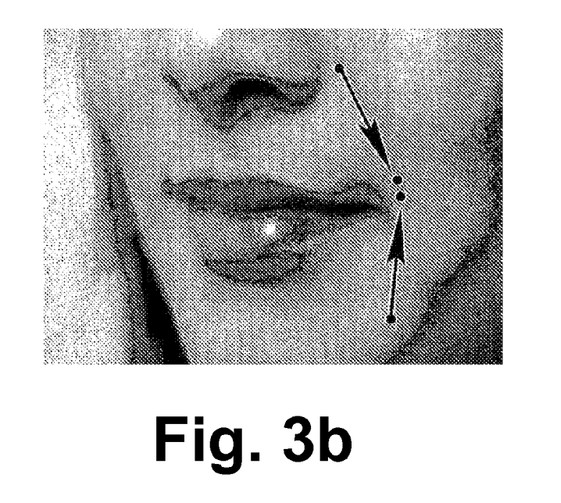

This method involves placing one electrode at the inferior position of the Nasolabial fold and one at the superior position. The electrodes are held in position for about 6 seconds, then travel towards each other with firm pressure until the electrodes are about 0.5 inches apart with a fold of tissue created therebetween, which should be done slowly with the stroke taking about 4 seconds. The tips are then held in that position for about 4 seconds. The above is repeated one more time, then the electrodes are placed just above the nasolabial fold parallel to the first strokes, and the stroke repeated two more times. During the application, the source is operated at a galvanic current of about 160 microamps, and at a frequency of about 10 Hz, and also with alternating tip polarity. FIG. 3a is an illustrative view of this application pattern. This comprises a first session. A second session identical to the first is performed after a rest period. Thereafter, sessions 3 and 4 would be identical in terms of electrode placement and strokes, but the source would be operated at a galvanic current of about 320 microamps, and at a frequency of about 7 Hz. Each session thereafter would be identical in terms of electrode placement and strokes but the source would be operated at a galvanic current of about 640 microamps and a frequency of about 3 Hz. FIG. 3b illustrates the pattern in practice.

This stroke in essence plumps the tissue, reducing the depth of the nasolabial fold, and promoting raising of the mouth and heightening of the cheek area.

In another embodiment of the invention, a method for plumping the lips is disclosed.

This method involves, beginning with the bottom lip, placing the two electrodes, side by side on the lip at the midline, with a spacing of about 0.25-0.5 inches. The two electrodes are then moved towards each other to compress the intervening lip tissue therebetween, and then the electrodes are held in position for about 8 seconds, then the two electrodes are moved laterally towards one corner of the mouth, and the compression and holding repeated three more times. Then the electrodes are returned to the midline, and the sequence repeated working to the opposite corner of the mouth. Then the same sequences are repeated for the upper lip.

Figure 4A:
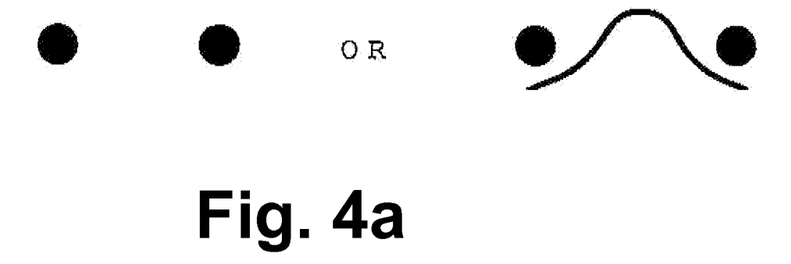
FIG. 4a is a view of an exemplary application pattern for promoting plumping of the lips and FIG. 4b is a view of human lips with the dots and lines illustrating the pattern as practiced for promoting plumping of the lips.
Figure 4B:
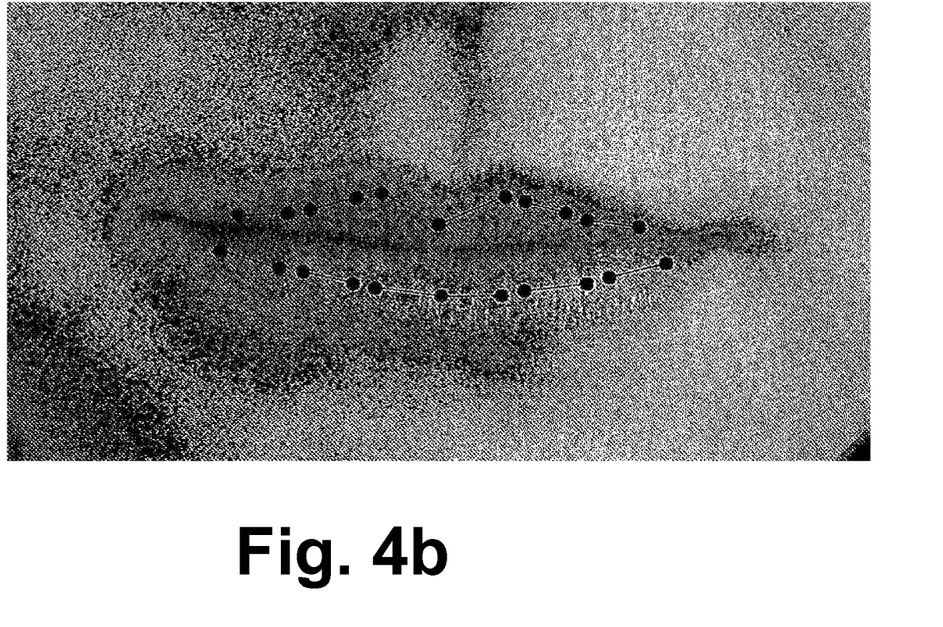

During the application, the source is operated at a galvanic current of about 160 microamps, and at a frequency of about 10 Hz, and also with alternating tip polarity. FIG. 4a is an illustrative view of this application pattern. This comprises a first session. A second session identical to the first is performed after a rest period. Thereafter, sessions 3 and 4 would be identical in terms of electrode placement and strokes, but the source would be operated at a galvanic current of about 320 microamps, and at a frequency of about 7 Hz. Each session thereafter would be identical in terms of electrode placement and strokes but the source would be operated at a galvanic current of about 640 microamps and a frequency of about 3 Hz. FIG. 4b illustrates the pattern in practice.

This stroke in essence causes blood to flow into the lips to provide fuller as well as redder lips, while also toning and strengthening the Labium Superius and Labium Inferius.

In another embodiment of the invention, a method for toning the Orbicularis Oris is disclosed.

This method involves placing the two electrodes, side by side outside of the vermillion border of the lips, that is, below the lip midline and along the Orbicularis Oris, with a spacing of about 0.5 inches. The two electrodes are then moved towards each other to compress the intervening tissue therebetween, and then the electrodes are help in position for about 8 seconds, then the two electrodes are moved laterally towards one corner of the mouth, and the compression and holding repeated three more times. Then the electrodes are returned to the midline, and the sequence repeated working to the opposite corner of the mouth. Then the same sequences are repeated above the upper lip along the Orbicularis Oris. When the corner of the mouth is reached, the electrodes are moved above and below the corner, to compress and gently raise the angle of the mouth.

Figure 5A:
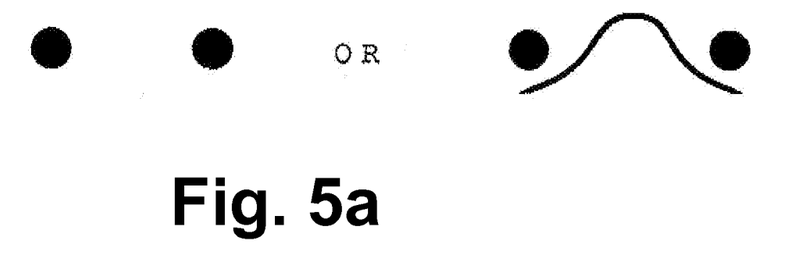
FIG. 5a is view of an exemplary application pattern for promoting toning of the Orbicularis Oris and FIG. 5b is a view of human lips with the dots, lines and arrows illustrating the pattern as practiced for promoting toning of the Orbicularis Oris.
Figure 5B:
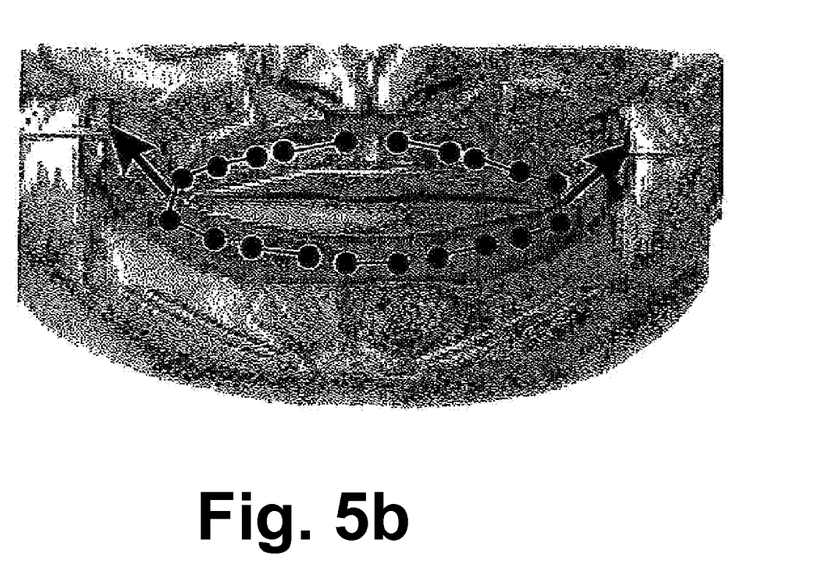

During the application, the source is operated at a galvanic current of about 160 microamps, and at a frequency of about 10 Hz, and also with alternating tip polarity. FIG. 5a is an illustrative view of this application pattern. This comprises a first session. A second session identical to the first is performed after a rest period. Thereafter, sessions 3 and 4 would be identical in terms of electrode placement and strokes, but the source would be operated at a galvanic current of about 320 microamps, and at a frequency of about 7 Hz. Each session thereafter would be identical in terms of electrode placement and strokes but the source would be operated at a galvanic current of about 640 microamps and a frequency of about 3 Hz. FIG. 5b illustrates the pattern in practice.

This stroke in essence reduces the appearance of vertical lines along the vermillion border, while also increasing the muscle tone of the Orbicularis Orbis, and also raises the angle of the mouth.

In another embodiment of the invention, an alternative method for reducing the depth of the Nasolabial fold is disclosed.

This method involves placing the two electrodes, side by side, one placed directly on the Nasolabial fold, the other placed just above the line of the fold, starting next to the nose and moving towards the jaw line, with a spacing of about 0.5 inches. The two electrodes are then moved towards each other to compress the intervening tissue therebetween, and then the electrodes are held in position for about 8 seconds, then the two electrodes are moved laterally towards the jaw line, and the compression and holding repeated three more times.

Figure 6A:
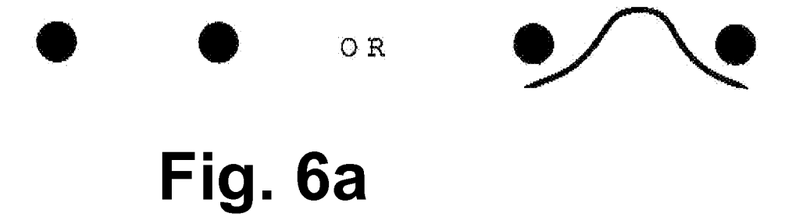
FIG. 6a is a view of an exemplary alternative application pattern for promoting nasolabial fold toning and FIG. 6b is a view of a human face with the dots and arrows illustrating the pattern as practiced for promoting nasolabile fold toning.
Figure 6B:
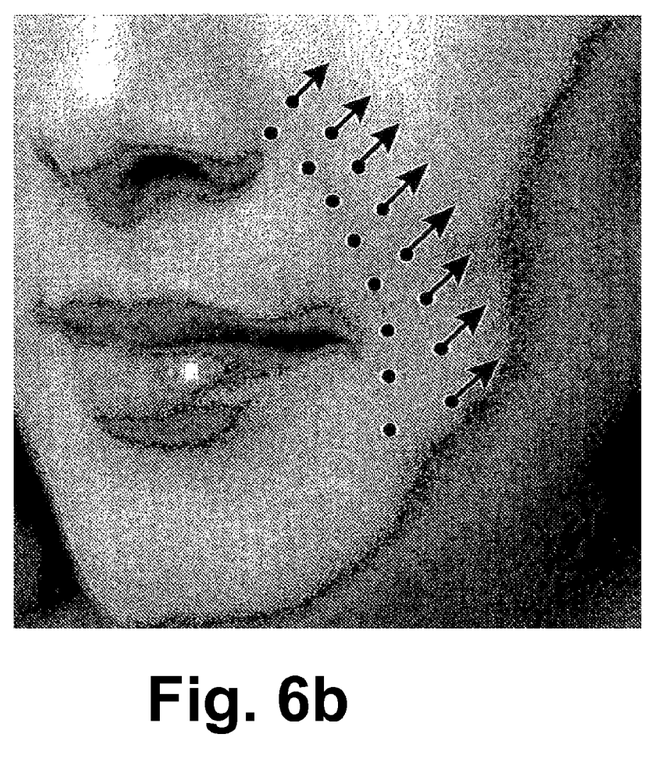

During the application, the source is operated at a galvanic current of about 160 microamps, and at a frequency of about 10 Hz, and also with alternating tip polarity. FIG. 6a is an illustrative view of this application pattern. This comprises a first session. A second session identical to the first is performed after a rest period. Thereafter, sessions 3 and 4 would be identical in terms of electrode placement and strokes, but the source would be operated at a galvanic current of about 320 microamps, and at a frequency of about 7 Hz. Each session thereafter would be identical in terms of electrode placement and strokes but the source would be operated at a galvanic current of about 640 microamps and a frequency of about 3 Hz. FIG. 6b illustrates the pattern in practice.

This stroke in essence promotes a reduction in the depth of the Nasolabial fold, heightens the cheek area and lessens and smoothes the smile line and cheek line.

In another embodiment of the invention, a method for toning the vermillion border is disclosed.

This method involves placing the two electrodes, side by side directly on the vermillion border of the upper lip, starting at one corner of the mouth, with a spacing of about 0.5 inches. The two electrodes are then moved towards each other to compress the intervening tissue therebetween, and then the electrodes are held in position for about 8 seconds, then the two electrodes are moved laterally towards the center of the mouth, and the compression and holding repeated until the center is reached. Then the electrodes are placed on the vermillion border starting at the opposite corner of the mouth and returned to the midline.

Figure 7A:
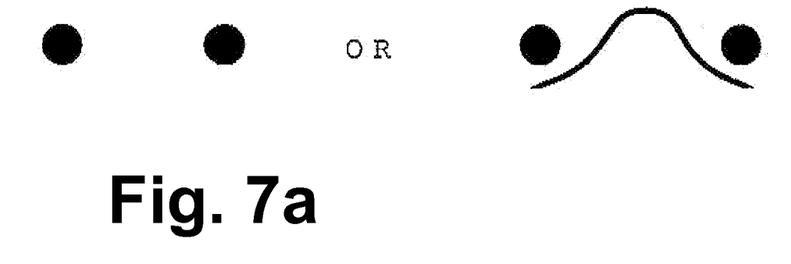
FIG. 7a is a view of an exemplary application pattern for promoting toning of the vermilion border and FIG. 7b is a view of human lips with the dots and lines illustrating the pattern as practiced for promoting toning of the vermillion border.
Figure 7B:
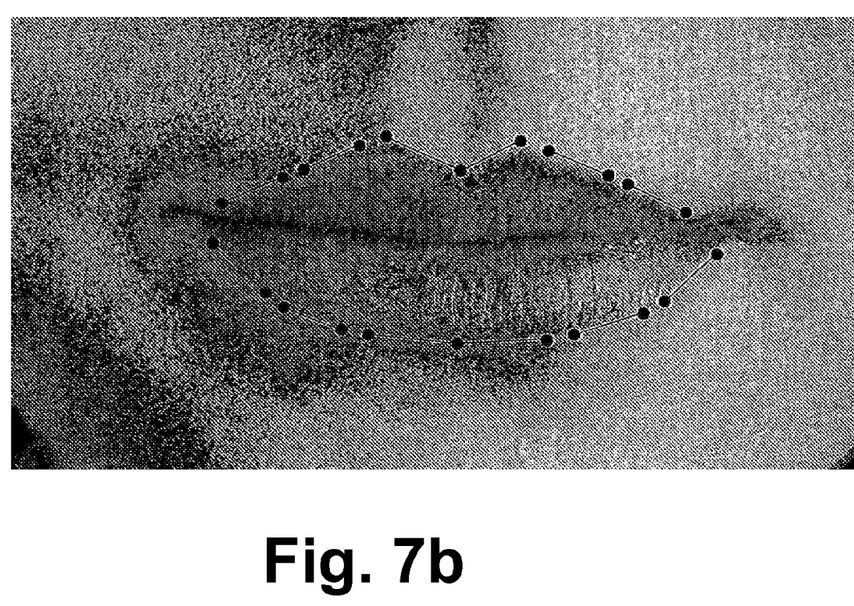

During the application, the source is operated at a galvanic current of about 160 microamps, and at a frequency of about 10 Hz, and also with alternating tip polarity. FIG. 7a is an illustrative view of this application pattern. This comprises a first session. A second session identical to the first is performed after a rest period. Thereafter, sessions 3 and 4 would be identical in terms of electrode placement and strokes, but the source would be operated at a galvanic current of about 320 microamps, and at a frequency of about 7 Hz. Each session thereafter would be identical in terms of electrode placement and strokes but the source would be operated at a galvanic current of about 640 microamps and a frequency of about 3 Hz. FIG. 7b illustrates the pattern in practice.

This stroke in essence reduces the appearance of vertical lines along the upper lip area, and increases the definition of the vermillion border.

In another embodiment of the invention, a method for toning the muscle of Tragus is disclosed.

This method involves placing one electrode tip near the ear, just inferior to the tragus. The second electrode is positioned about 1 inch from the first electrode, and the moved towards the first electrode, to compress about 0.5 inches of tissue therebetween and held for about 8 seconds. The first electrode tip would then move outwards along the tragus, and the second electrode repositioned about 1 inch away, and the compression of the tissue therebetween repeated. This continues until the last stroke is in line with the top of the ear.

Figure 8A:
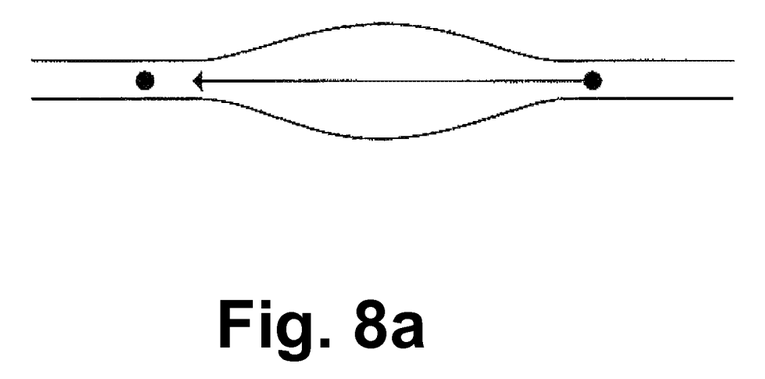
FIG. 8a is a view of an exemplary application pattern for promoting toning of the Muscle of Tragus and FIG. 8b is a view of a side of a human head with the arrows and dots illustrating the pattern as practiced for promoting toning of the Muscle of Tragus.
Figure 8B:
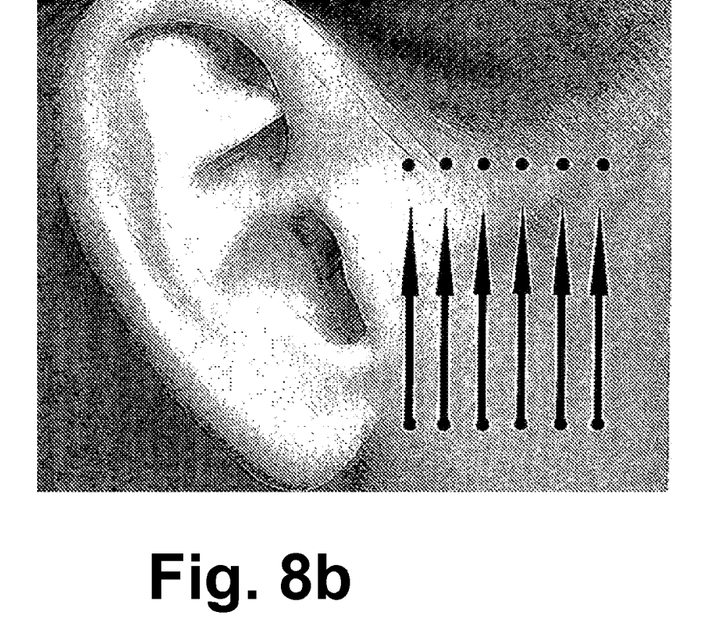

During the application, the source is operated at a galvanic current of about 160 microamps, and at a frequency of about 10 Hz, and also with alternating tip polarity. FIG. 8a is an illustrative view of this application pattern. This comprises a first session. A second session identical to the first is performed after a rest period. Thereafter, sessions 3 and 4 would be identical in terms of electrode placement and strokes, but the source would be operated at a galvanic current of about 320 microamps, and at a frequency of about 7 Hz. Each session thereafter would be identical in terms of electrode placement and strokes but the source would be operated at a galvanic current of about 640 microamps and a frequency of about 3 Hz. FIG. 8b illustrates the pattern in practice.

This stroke in essence seeks to shorten the muscle fibers of the muscle of tragus, to promote a reduction in the appearance of folds anterior to the ear.

In another embodiment of the invention, a method for relaxing the nasalis is disclosed.

This method involves placing the two electrodes, side by side directly on the belly of the nasalis, about ⅛th inches apart. Both tips are then moved away from each other, one moving towards the muscle origin, the other to the muscle insertion, with firm pressure. The stroke is then repeated just above the area of the first stroke, and the repeated in an area just below the area of application of the first stroke.

Figure 9A:
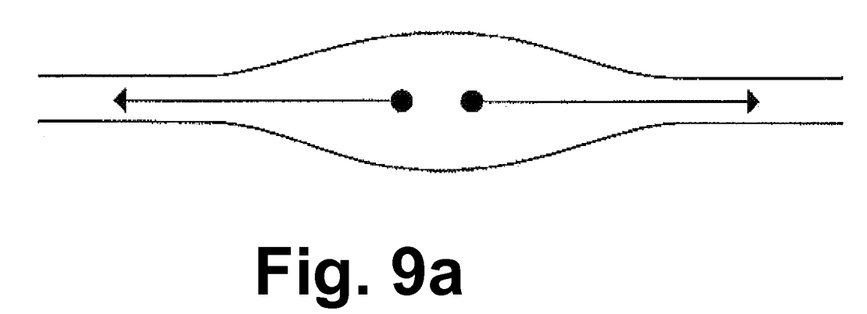
FIG. 9a is a view of an exemplary application pattern for promoting relaxation of the nasalis and FIG. 9b is a view of a human face with the arrows illustrating the pattern as practiced for promoting relaxation of the nasalis.
Figure 9B:
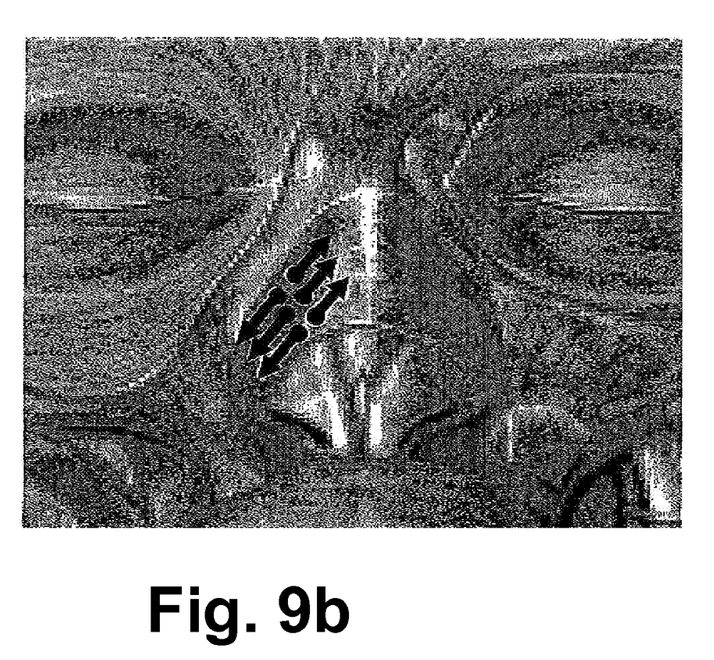

During the application, the source is operated at a galvanic current of about 320 microamps, and at a frequency of about 70 Hz, and also with alternating tip polarity. FIG. 9a is an illustrative view of this application pattern. This comprises a first session. Three more sessions identical to the first are performed, each after a rest period. Each session thereafter would be identical in terms of electrode placement and strokes but the source would be operated at a galvanic current of about 640 microamps and a frequency of about 90 Hz. FIG. 9b illustrates the pattern in practice.

This stroke in essence reduces the appearance of lines along the bridge of the nose and promotes a lessening in tension of the nasalis.

In another embodiment of the invention, a method for toning the Platysma is disclosed.

This method involves placing one electrode along the vertical center line of the neck at an inferior position, and the other at a superior position. The inferior electrode tip is then moved towards the superior, until the are about 0.5 inches apart, with a fold of skin in between and held for 8 seconds. The stroke is repeated for eight times and then the two electrodes are positioned parallel to the center stroke, but moved towards the side of the neck, moving progressing laterally towards the side of the neck. At each move, the stroke sequence is repeated. Thereafter, the electrodes are moved to the other side of the neck and the stroke repeated, moving away from the center line towards the other side of the neck.

Figure 10A:
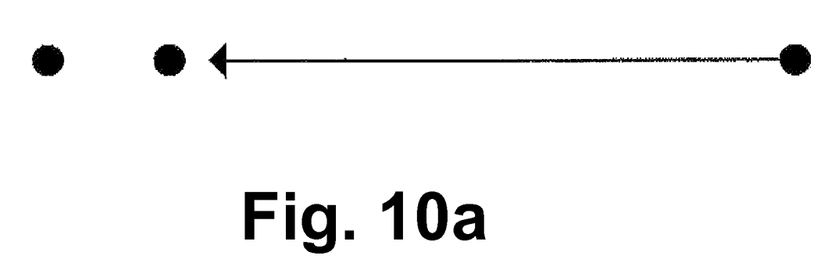
FIG. 10a is a view of an exemplary application pattern for promoting toning of the Platysma and FIG. 10b is a view of a human neck with the arrows illustrating the pattern as practiced for promoting toning of the Platysma.
Figure 10B:
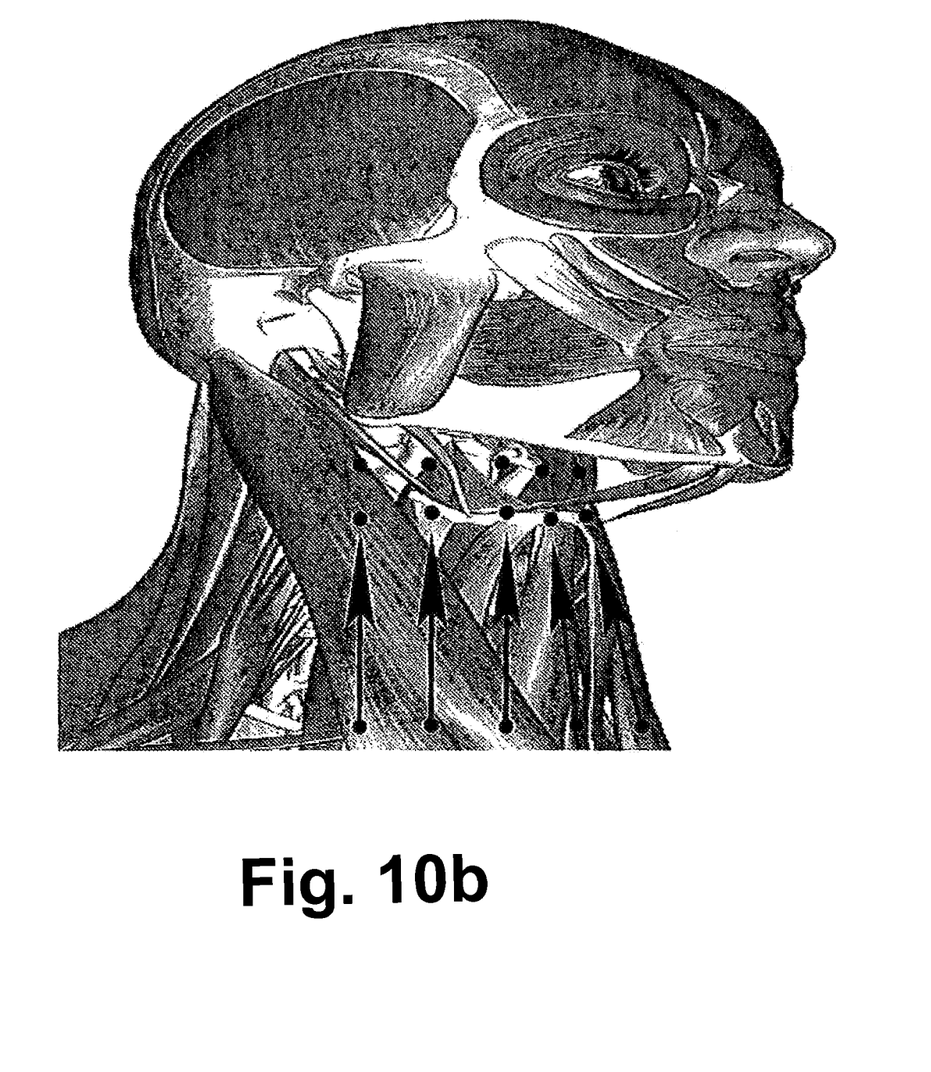

During the application, the source is operated at a galvanic current of about 160 microamps, and at a frequency of about 10 Hz, and also with alternating tip polarity. FIG. 10a is an illustrative view of this application pattern. This comprises a first session. A second session identical to the first is performed after a rest period. Thereafter, sessions 3 and 4 would be identical in terms of electrode placement and strokes, but the source would be operated at a galvanic current of about 320 microamps, and at a frequency of about 7 Hz. Each session thereafter would be identical in terms of electrode placement and strokes but the source would be operated at a galvanic current of about 640 microamps and a frequency of about 3 Hz. FIG. 10b illustrates the pattern in practice.

This stroke in essence reduces the appearance of sagging skin, and to promote strengthening of the dermal layer with increased circulation.

The methods herein described are preferably practiced after the target areas are appropriately cleansed, to improve conductivity of the galvanic current, and absorption of the liquid solutions.

Figure 11:
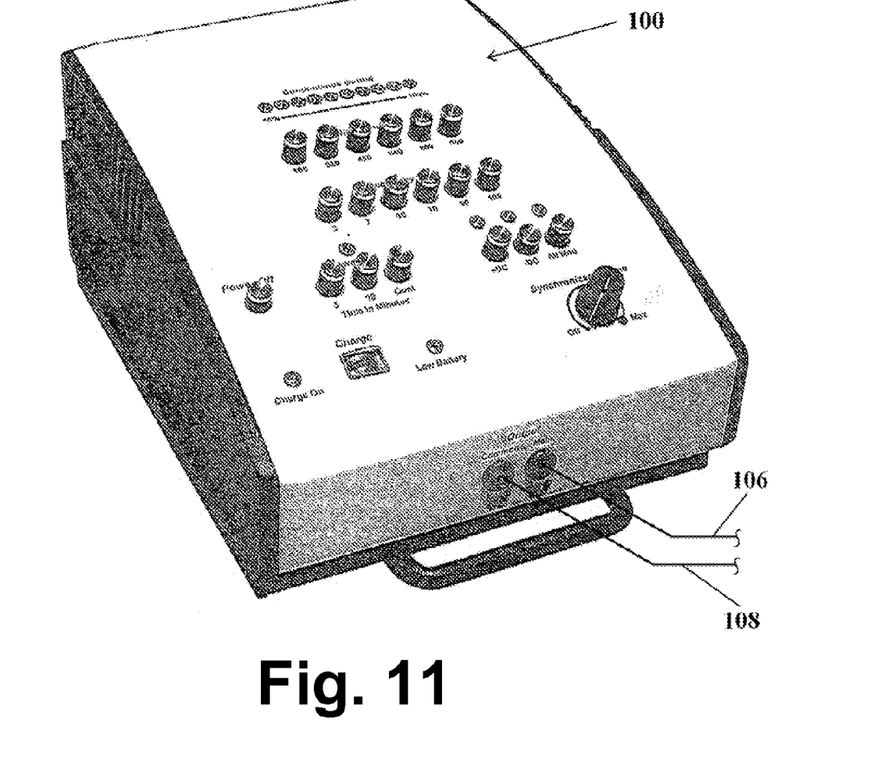
FIG. 11 is a schematic illustration of an apparatus for providing a source of galvanic current connected to a pair of electrodes.

Various devices are available which may be used to apply the galvanic current discussed herein, such as the Microlift, made by Myo Inc. The MicroLift unit 100, shown in FIG. 11, is a high quality machine with an output that is accurate within +/−5 percent. The unit weights 4 pounds, and provide galvanic current in the range of 160 to 960 Microamps in six preset levels. The frequency delivered is in the range of 3 to 100 Hz, in 6 preset levels. The unit has a timer, pushbutton selectable for 5 minute, 10 minute, and continuous operation. The output wave can be modified square DC bi-phasic. Polarity changes follow at 2 second intervals This device may be adjusted for obtaining different currents, different frequencies and different polarities. The duration of one or the other polarity may be adjusted.

Figure 12:
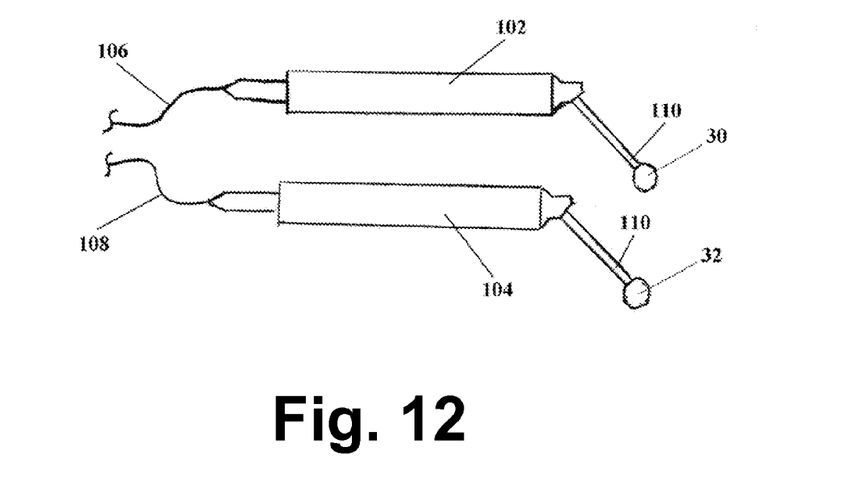
FIG. 12 is a view of two electrodes usable with the apparatus of FIG. 11 in practicing the methods of the invention.

The instrument typically employs two electrodes 102, 104, as shown in FIG. 12, which are connected by conducting wires 106, 108 to the apparatus 100 and a cotton-wrapped tip 30, 32 may be inserted in the tip 110 of each electrode until the cotton portion makes contact with the metal of the electrode. The cotton portions are dipped into the desired solution to form moistened tips and are thereafter applied to the skin of the face in the manner of the methods described herein. The moistened tips are continually moistened, to keep the tips moist.

The method described herein involves certain predetermined movements of the moistened tips of the electrodes while pressed against the skin so as to relax certain muscles, strengthen and tighten other muscles and to tone, plump or tighten the tissues overlying the muscles for enhanced cosmetic effects.

The methods described above stimulate muscles, while improving blood circulation and thus nourishment of the muscles and facial tissues. The moistened tips, as earlier described, are continually moistened with a liquid solution of positively and negatively charged particles. Various ingredients may be used in such liquid solution, such as collagen, elastin and other active ingredients found naturally in the human body, and which are only being replaced for use by the body. Nutritious substances containing proteins, fats, carbohydrates, water and other trace elements may also be introduced into the tissues by use of the moistened tips in the manner described. Glycerin and other emollients may be introduced. All substances mentioned, and others, not specifically mentioned, may be introduced, depending upon the state of facial tone and extent of aging. All such substances must be ionized so as to be able to penetrate by the concept of iontophoresis into the skin. Liquid solutions that are ionized and therefore penetrated into the epidermis and dermis will have a longer effect than liquid solutions that only stay on the surface of the skin, such as moisturizers.

The invention has been described in detail with particular reference to preferred embodiments thereof, but it will be understood that variations and modifications can be effected within the spirit and scope of the invention.

What is claimed is:

1. A method of toning the muscles and tissues of the human face comprising:
    selecting muscles of the human face,
    stimulating specific motor nerves to cause contraction of the selected muscles of the human face using a pair of electrodes connected to a source of predetermined galvanic current, operable at a plurality of multiple user selected microcurrent power levels and frequencies,
    selecting a first specific combination of a microcurrent power level and a frequency for stimulating the selected muscles,
    energizing the electrodes,
    pressing the pair of electrodes against the skin of the human face at two preselected positions adjacent the selected muscles and while pressed against the skin,
    moving a first electrode in a first programmed pattern while either holding the second electrode in position or moving a second electrode in a second programmed pattern adjacent to the selected muscles, such that the first selected microcurrent and frequency pass into the selected muscles to stimulate the muscle and tissue located between the pair of electrodes, and,
    repeating the pressing and moving of the pair of electrodes using a second selected microcurrent power level and frequency, and optionally, repeating the pressing and moving again using a third selected microcurrent power level and frequency, the repeating and moving of the electrodes at the selected plurality of microcurrent and frequency combinations variably stimulating the muscle and tissue located between the pair of electrodes for promoting toning of the selected muscle.

2. The method of claim 1 wherein the electrodes have moistening tips, and further comprising moving the electrodes relative to each other in the preselected pattern multiple times, while continually moistening the tips of the electrodes with a liquid solution of positively and negatively charged particles for promoting diffusion of the liquid solution into the skin.

3. The method of claim 1, wherein the pressing and moving steps comprise placing the first electrode at a lateral corner just below an eye, placing the second electrode at a medial inferior corner just below the eye and with very light pressure, moving the first electrode towards the midline located electrode and then back to the starting position with no pressure, and repeating, each complete back and forth pass to be completed within about 0.5 seconds.

4. The method of claim 3 wherein the first specific combination of a microcurrent power level and a frequency for stimulating the selected muscles is obtained by operating the source at a galvanic current of about 160 microamps, and at a frequency of about 10 Hz, and also with alternating tip polarity.

5. The method of claim 4 wherein the second specific combination of a microcurrent power level and a frequency for stimulating the selected muscles is obtained by operating the source at a galvanic current of about 320 microamps, and at a frequency of about 7 Hz.

6. The method of claim 1 wherein the pressing and moving steps comprise placing the first electrode at an origin of a temporalis muscle and the second electrode at an insertion of the muscle, holding the electrodes in position for about 6 seconds, then moving one electrode upwardly towards the other electrode with light pressure at a speed of about 0.5 inches per second, until the electrodes are about 0.5 inches apart with a fold of tissue created therebetween, then holding the electrodes in that position for about 4 seconds.

7. The method of claim 6 further comprising moving the electrodes about 0.25 inches and repeating.

8. The method of claim 7 wherein the first specific combination of a microcurrent power level and a frequency for stimulating the selected muscles is obtained by operating the source at a galvanic current of about 160 microamps, and at a frequency of about 10 Hz, and also with alternating tip polarity.

9. The method of claim 8 wherein the second specific combination of a microcurrent power level and a frequency for stimulating the selected muscles is obtained by operating the source at a galvanic current of about 320 microamps, and at a frequency of about 7 Hz.

10. The method of claim 9 wherein the third specific combination of a microcurrent power level and a frequency for stimulating the selected muscles is obtained by operating the source at a galvanic current of about 640 microamps and a frequency of about 3 Hz.

11. The method of claim 1 wherein the pressing and moving steps comprise placing the first electrode at the inferior position of the Nasolabial fold and the second electrode at the superior position, holding the electrodes in position for about 6 seconds, then moving the electrodes towards each other with firm pressure until the electrodes are about 0.5 inches apart with a fold of tissue created therebetween, holding the electrodes in that position for about 4 seconds, and repeating, this comprising a stroke, then placing the electrodes just above the nasolabial fold parallel to the stroke, and repeating the stroke two more times.

12. The method of claim 1 wherein the pressing and moving steps comprise placing the two electrodes, side by side on a lower lip at a midline thereof, with a spacing of about 0.25-0.5 inches, then moving the two electrodes towards each other to compress the intervening lip tissue therebetween, and holding the electrodes in position for about 8 seconds, comprising a compression stroke, then moving the two electrodes laterally towards one corner of the mouth, and repeating the compression stroke, and then repeating until the corner of the mouth is reached, and then moving the electrodes back to the midline, and repeating the compression strokes working towards an opposite corner of the mouth, and then moving to the upper lip and repeating the same compression strokes and movements on the upper lip.

13. The method of claim 1 the pressing and moving steps comprise further comprising placing the two electrodes, side by side outside of a vermillion border of the lips, and below the lower lip midline, along the Orbicularis Oris, with a spacing of about 0.5 inches, moving the two electrodes towards each other to compress the intervening tissue therebetween, and then holding the electrodes in position for about 8 seconds, comprising a compression stroke, then moving the two electrodes laterally towards one corner of the mouth, and repeating the compression stroke three more times, then returning the electrodes to the midline, and repeating the compression strokes and movements, working to the opposite corner of the mouth, and then placing the electrodes side by side outside of the vermillion border above the upper lip and repeating the compression strokes and movements, working to both corners of the mouth, and the placing the two electrodes above and below a first corner of the mouth and performing a compression stroke, the moving the electrodes to the opposite corner of the mouth and repeating the compression stroke.

14. The method of claim 1 wherein the pressing and moving steps comprise placing the two electrodes, side by side directly on the vermillion border of the upper lip, starting at one corner of the mouth, with a spacing of about 0.5 inches, and moving the two electrodes towards each other to compress the intervening tissue therebetween, and then holding the electrodes in position for about 8 seconds, comprising a compression stroke, then moving the two electrodes laterally towards a center of the mouth, and repeating the compression stroke and movement until the center is reached, then placing the two electrodes on the vermillion border starting at an opposite corner of the mouth and repeating the compression and movements until the center.

15. The method of claim 1 wherein the pressing and moving steps comprise placing the two electrodes, side by side, the first electrode placed directly on a Nasolabial fold, the second electrode placed just above a line of the fold, starting next to the nose, with a spacing of about 0.5 inches, then moving the electrodes towards each other to compress the intervening tissue therebetween, and then holding the electrodes in position for about 8 seconds, comprising a compression stroke, then the two electrodes are moved laterally towards the jaw line, and the compression stroke and moving are repeated until an end of the fold is reached.

16. The method of claim 1 wherein the pressing and moving steps comprise placing one electrode near the ear, just inferior to the muscle of tragus, placing the second electrode about 1 inch from the first electrode, and then moving the second electrode towards the first electrode to compress about 0.5 inches of tissue therebetween and then holding for about 8 seconds, comprising a compression stroke, the moving the first electrode tip outwards along the tragus, and repositioning the second electrode about 1 inch away, and repeating the compression stroke, and repeating the movement and compression stroke until the electrode are in line with a top of the ear.

17. The method of claim 1 wherein the pressing and moving steps comprise placing the two electrodes, side by side directly on a belly of the nasalis, about ⅛th inches apart, then moving the electrodes simultaneously away from each other, one electrode moving towards an origin of the muscle, the other electrode moving to the muscle insertion, with firm pressure, comprising a stroke, and repeating the stroke with the two electrode placed just above an area of the first stroke, and then repeating the stroke in an area just below the area of the first stroke.

18. The method of claim 1 wherein the pressing and moving steps comprise placing the first electrode along a vertical center line of the neck at an inferior position, and the second electrode at a superior position, then moving the first electrode towards the second electrode until the electrodes are about 0.5 inches apart, with a fold of skin in between, and then holding the electrodes for 8 seconds, comprising a stroke, and the repeating the stroke eight times and then moving the two electrodes to positions parallel to the center stroke, in a direction towards a side of the neck, and repeating the stroke 8 times, and moving progressing laterally towards the side of the neck, and the moving the electrodes back to the center line of the neck and repeating the strokes moving towards an opposite side of the neck.

* * * * *